United States Patent [19] — Fryer et al.

[11] 4,436,662
[45] Mar. 13, 1984

[54] PYRROLO[3,4-D][2]BENZAZEPINONES

[75] Inventors: Rodney I. Fryer, North Caldwell; Eugene J. Trybulski, Parsippany; Armin Walser, West Caldwell, all of N.J.

[73] Assignee: Hoffmann-La Roche Inc., Nutley, N.J.

[21] Appl. No.: 481,021

[22] Filed: Mar. 31, 1983

Related U.S. Application Data

[63] Continuation-in-part of Ser. No. 393,142, Jun. 28, 1982, abandoned, which is a continuation-in-part of Ser. No. 379,400, May 18, 1982.

[51] Int. Cl.$^3$ .............................................. C07D 487/02
[52] U.S. Cl. .................................. 260/245.7; 424/274; 424/244; 562/493; 568/807; 568/425; 548/461; 260/465 K; 260/465 G
[58] Field of Search ........................................ 260/245.7

[56] References Cited

U.S. PATENT DOCUMENTS 3,947,585  3/1976  Gschwend ........................ 424/250
4,257,946  3/1981  Walser ............................. 260/245.7
4,354,973  10/1982  Fryer et al. ....................... 260/245.7

FOREIGN PATENT DOCUMENTS 45519  2/1982  European Pat. Off. .

Primary Examiner—Donald G. Daus
Assistant Examiner—William A. Teoli, Jr.
Attorney, Agent, or Firm—Jon S. Saxe; Bernard S. Leon; Frank P. Hoffman

[57] ABSTRACT

The present invention relates to compounds of the formula

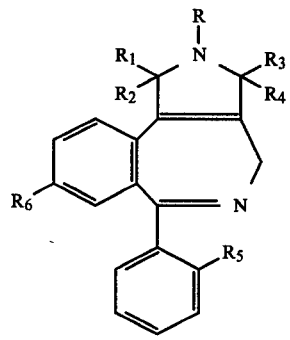

wherein $R_1$ and $R_3$ are selected from the group consisting of hydrogen, lower alkyl, hydroxy, lower alkoxy or acyloxy and $R_2$ and $R_4$ are hydrogen or $R_1$ and $R_2$ and/or $R_3$ and $R_4$ taken together are oxo groups with the proviso that at least one oxo group is present; R is selected from the group consisting of hydrogen, lower alkyl, $C_2$ to $C_7$ carboxylic acids and the esters and amides thereof, hydroxy $C_2$ to $C_7$ alkyl and amino $C_2$ to $C_7$ alkyl or mono- or di-lower alkyl amino $C_2$ to $C_7$ alkyl; $R_5$ is halogen or hydrogen; and $R_6$ is halogen with the proviso that when $R_1$ or $R_3$ is hydroxy, lower alkoxy or acyloxy, then R is lower alkyl or hydrogen and the N-oxides and the pharmaceutically acceptable salts thereof.

17 Claims, No Drawings

PYRROLO[3,4-D][2]BENZAZEPINONES

This application is a continuation-in-part of Ser. No. 393,142, filed on June 28, 1982, now abandoned, which in turn is a continuation-in-part of Ser. No. 379,400, filed on May 18, 1982.

DESCRIPTION OF INVENTION

The present invention relates to compounds of the formula

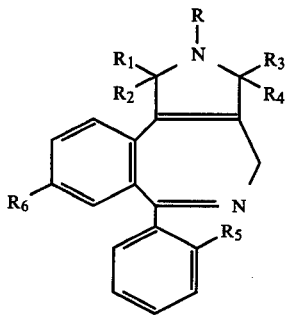

wherein $R_1$ and $R_3$ are selected from the group consisting of hydrogen, lower alkyl, hydroxy, lower alkoxy or acyloxy and $R_2$ and $R_4$ are hydrogen or $R_1$ and $R_2$ and/or $R_3$ and $R_4$ taken together are oxo groups with the proviso that at least one oxo group is present; R is selected from the group consisting of hydrogen, lower alkyl, $C_2$ to $C_7$ carboxylic acids and the esters and amides thereof, hydroxy $C_2$ to $C_7$ alkyl and amino $C_2$ to $C_7$ alkyl or mono- or di-lower alkyl amino $C_2$ to $C_7$ alkyl; $R_5$ is halogen or hydrogen; and $R_6$ is halogen with the proviso that when $R_1$ or $R_3$ is hydroxy, lower alkoxy or acyloxy, then R is lower alkyl or hydrogen and the N-oxides and the pharmaceutically acceptable salts thereof.

The compounds exhibit activity as sedative and anxiolytic agents.

By the term "halogen" is meant bromo, chloro or fluoro, i.e., having an atomic number not greater than 35, except as limited herein.

By the term "lower alkyl" is meant both straight and branched chain $C_1$ to $C_7$ hydrocarbon groups, preferably $C_1$ to $C_4$ carbon-hydrogen radicals, such as methyl, ethyl, propyl, isopropyl and the like.

By the term "acyloxy" is meant a radical derived from an organic acid by the removal of the hydrogen atom, i.e., radicals of the formula

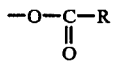

wherein R is $C_1$ to $C_6$ alkyl, phenyl or hydrogen, e.g., acetyl, propionyl, butyryl, benzoyl, etc.

By the term "carboxylic acids and the esters and amides thereof" is meant radicals of the formula —$C_1$ to $C_6$ lower alkyl- $COR_{21}$ where $R_{21}$ is hydroxy, lower alkoxy, amino or amino which is mono- or di-substituted by lower alkyl.

The expression "pharmaceutically acceptable salts" is used to include salts with both inorganic and organic pharmaceutically acceptable acids, such as sulfuric acid, hydrochloric acid, nitric acid, methanesulfonic acid and p-toluenesulfonic acid. Such salts can be formed quite readily by those skilled in the art with the prior art and the nature of the compounds to be placed in salt form in view.

Preferred compounds within the scope of the present invention are those of the formula I, i.e., the Schiff bases. Further preferred compounds are those of the formula I wherein $R_3$ and $R_4$ taken together are an oxo group. Still further preferred compounds are those of formula I wherein $R_2$ is hydrogen, $R_1$ is preferably hydrogen or lower alkyl, more preferably hydrogen or methyl. The preferred meaning of R is hydrogen or lower alkyl, more preferably hydrogen or methyl. $R_5$ and $R_6$ are preferably halogen.

From the above it follows that an especially preferred group of compounds within the scope of the present invention are those of formula I, wherein R and $R_1$ are hydrogen or lower alkyl, preferably methyl, $R_2$ is hydrogen, $R_3$ and $R_4$ taken together are an oxo group and $R_5$ and $R_6$ are halogen.

Preferred compounds are those of the formulas:

8-chloro-6-(2-fluorophenyl)-3,4-dihydropyrrolo[3,4-d][2]benzazepin-1(2H)-one 8-chloro-6-(2-chlorophenyl)-3,4-dihydropyrrolo[3,4-d][2]benzazepin-1(2H)-one 8-chloro-3,4-dihydro-6-phenylpyrrolo[3,4-d][2]benzazepin-1(2H)-one 8-chloro-6-(2-chlorophenyl)-3,4-dihydro-2-methylpyrrolo[3,4-d][2]benzazepin-1(2H)-one 8-chloro-6-(2-chlorophenyl)-1,4-dihydro-1-hydroxypyrrolo[3,4-d][2]benzazepin-3(2H)-one 8-chloro-6-(2-chlorophenyl)-3,4-dihydro-3-hydroxypyrrolo[3,4-d][2]benzazepin-1(2H)-one 8-chloro-6-(2-chlorophenyl)pyrrolo[3,4-d][2]benzazepin-1,3-(2H,4H)-dione 8-chloro-6-(2-chlorophenyl)-1,4-dihydropyrrolo[3,4-d][2]benzazepin -3(2H)-one-5-oxide 8-chloro-6-(2-chlorophenyl)-3,4-dihydropyrrolo[3,4-d][2]benzazepin-1(2H)-one-5-oxide 8-chloro-6-(2-chlorophenyl)-1-ethyl-1,4-dihydropyrrolo[3,4-d][2]benzazepin-3(2H)-one 8-chloro-6-(2-chlorophenyl)-1,4-dihydro-1-methyl-3-oxo-2H-pyrrolo[3,4-d][2]benzazepine-2-acetic acid methyl ester and 8-chloro-6-(2-chlorophenyl)-1,4-dihydro-1-methyl-3-oxo-2H-pyrrolo[3,4-d][2]benzazepine-2-acetamide.

Especially preferred compounds are those of the formulas:

8-chloro-6-(2-fluorophenyl)-1,4-dihydropyrrolo[3,4-d][2]benzazepin-3(2H)-one 8-chloro-1,4-dihydro-6-phenylpyrrolo[3,4-d][2]benzazepin-3(2H)-one 8 -chloro-6-(2-chlorophenyl)-1,4-dihydro-1,2-dimethylpyrrolo[3,4-d][2]benzazepin-3(2H)-one and 8-chloro-6-(2-chlorophenyl)-1,4-dihydro-2-(2-hyroxyethyl)-1-methylpyrrolo[3,4-d][2]benzazepin-3(2H)-one.

The most preferred compounds are those of the formulas:

8-chloro-6-(2-chlorophenyl)-1,4-dihydropyrrolo[3,4-d][2]benzazepin-3(2H)-one 8-chloro-6-(2-chlorophenyl)-1,4-dihydro-1-methylpyrrolo[3,4-d][2]benzazepin-3(2H)-one and 8-chloro-6-(2-chlorophenyl)-1,4-dihydro-2-methylpyrrolo[3,4-d][2]benzazepin-3(2H)-one.

The compounds of formula I, the N-oxides and the pharmaceutically acceptable salts thereof can be prepared by a process which comprises:

(a) for preparing compounds of the formula I above wherein $R_1$ or $R_3$ is hydrogen or lower alkyl and the remaining substituents are as above and the N-oxides thereof, by oxidizing a compound of the formula

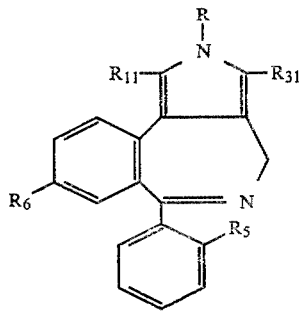

$$\text{II}$$

wherein one or $R_{11}$ and $R_{31}$ is hydrogen and the other is hydrogen or lower alkyl and R, $R_5$ and $R_6$ are as above with a peracid, or (b) for preparing compounds of the formula I above wherein $R_1$ or $R_3$ is hydroxy and the remaining substituents are as above or $R_1$ and $R_2$ and/or $R_3$ and $R_4$, respectively, are, when taken together, oxo groups and the remaining symbols are as above, by oxidizing a compound of formula I wherein $R_1$ or $R_3$ is hydrogen and the remaining substituents are as above, or by oxidizing a compound of the formula II above wherein $R_{11}$ and $R_{31}$ are hydrogen, with a lead (IV) carboxylate in the presence of a strong acid, or (c) for preparing compounds of the formula I above wherein $R_1$ or $R_3$ is acetoxy and the remaining substituents are as above, by treating a compound of the formula I wherein $R_1$ or $R_3$ is hydrogen and the remaining substituents are as above, or by treating a compound of the formula II above wherein $R_{11}$ and $R_{31}$ are hydrogen, with lead tetraacetate in acetic acid, or (d) for preparing compounds of the formula I above wherein $R_1$ or $R_3$ is acyloxy and the remaining substituents are as above, by treating a compound of formula I wherein $R_1$ or $R_3$ is hydroxy and the remaining substituents are as above, with a carboxylic anhydride in the presence of a base, or (e) for preparing compounds of the formula I above wherein $R_1$ or $R_3$ is lower alkoxy and the remaining substitutents are as above, by treating a compound of formula I wherein $R_1$ or $R_3$ is acyloxy or hydroxy and the remaining substituents are as above, or treating a compound of the formula

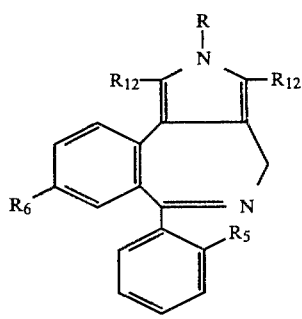

$$\text{III}$$

wherein $R_{12}$ is acetoxy and R, $R_5$ and $R_6$ are as above with a lower alkanol in the presence of a strong acid, or (f) for preparing compounds of the formula I above wherein $R_1$ or $R_3$ is hydrogen or alkyl and the remaining substituents are as above, desoxygenating an N-oxide of the formula

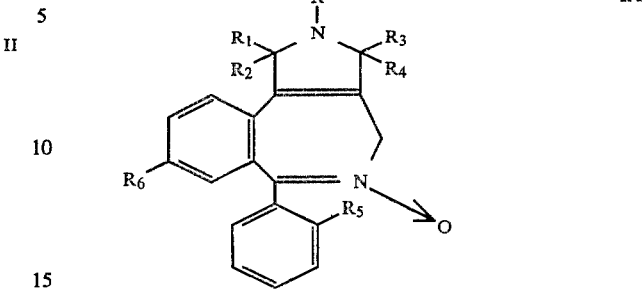

$$\text{IA}$$

wherein R, $R_2$, $R_4$, $R_5$ and $R_6$ are as above and $R_1$ and $R_3$ are hydrogen and (g) converting a compound of formula I into a pharmaceutically acceptable salt of a compound of formula I into another pharamaceutically acceptable salt.

The oxidation of a compound of formula II with a peracid according to process embodiment (a) of the present process is performed in a manner known per se. Suitable peracids for this oxidation step are peracids such as m-chloroperbenzoic acid, pertrifluoroacetic acid and the like. Depending on the reaction conditions used, one will obtain either the corresponding compounds of formula I or the N-oxides thereof. For obtaining the compounds of formula I, the reaction is expeditiously performed in a lower carboxylic acid such as acetic acid, trifluoroacetic acid, propionic acid and the like or in a mixture of such a carboxylic acid with a suitable inert solvent such as a chlorinated hydrocarbon, e.g., methylene chloride, an aromatic hydrocarbon, e.g., benzene, toluene, and the like, in the presence of a strong mineral acid such as sulfuric acid and the like. In case a corresponding N-oxide is desired, the reaction is conveniently performed in a suitable inert solvent such as a chlorinated hydrocarbon, e.g., methylene chloride, or an aromatic hydrocarbon, e.g., benzene, toluene and the like, in the absence of a strong mineral acid. The oxidation of a compound of formula II is preferably performed at a temperature between about 0° C. and about room temperature. It should be noted that a mixture of the 1-oxo and 3-oxo compounds will be obtained when in the starting material of formula II both $R_{11}$ and $R_{31}$ are hydrogen. In case the oxidation is performed under strong acidic conditions, the 3-oxo compound will predominate whereas the 1-oxo compound will be the predominant product when the reaction is performed in the absence of a strong mineral acid. The mixture obtained can be separated according to standard methods such as fractional crystallization and chromatography.

The oxidation in accordance with process embodiment (b) of the present process is also performed according to methods known per se. In this oxidation, lead (IV) carboxylates such as lead (IV) trifluoroacetate in an inert solvent such as chlorinated hydrocarbons such as methylene chloride or chloroform, and the like in the presence of a strong acid such as trifluoroacetic acid and the like can suitably be used. The reaction is preferably performed in a temperature range of from about 0° C. to about room temperature. In the case of a compound of formula II wherein $R_{11}$ and $R_{31}$ are hydrogen, a mixture of the 1-hydroxy-3-oxo, the 3-hydroxy-1-oxo and 1,3-dioxo compounds is obtained. The mixture thus obtained can be separated by standard chromatographic procedures.

Also, the reaction in accordance with process embodiment (c) of the present process is performed according to known methods. Thus, the starting material can be reacted with lead tetraacetate in acetic acid, preferably at about room temperature. Here again, a mixture of the 1-acetoxy-3-oxo and 3-acetoxy-1-oxo compounds will be obtained in case a compound of formula II wherein $R_{11}$ and $R_{31}$ are hydrogen is used as starting material. The mixture obtained can be separated by standard chromatographic procedures.

The reaction of a compound of formula I wherein $R_1$ or $R_3$ is hydroxy with a carboxylic acid anhydride in accordance with process embodiment (d) of the present process is also performed in a manner known per se, preferably in the presence of a base such as pyridine, dimethylaminopyridine, N-methylpiperidine and the like. Inert solvents which can be used in this reaction are chlorinated hydrocarbons such as methylene chloride, ethers such as tetrahydrofuran, and the like. The reaction is conveniently performed at a temperature in the range of about 0° C. to about room temperature.

The etherification in accordance with process embodiment (e) of the present process is performed in a manner known per se, expediently by reacting a compound of formula I wherein $R_1$ or $R_3$ is acyloxy, preferably acetoxy, with an excess of a lower alkanol containing a catalytic amount of a strong acid such as methane sulfonic acid and the like. This reaction is preferably at a temperature between about 0° C. and about room temperature.

The desoxygenation in accordance with process embodiment (f) of the present process is also performed according to known methods, conveniently by treating a compound of the formula IA with a desoxygenating agent such as phosphorous trichloride or triphenylphosphine in an inert solvent such as chlorinated hydrocarbons, e.g., methylene chloride, aromatic hydrocarbons, e.g., toluene, ethers, e.g., tetrahydrofuran, and the like at a temperature between about room temperature and the reflux temperature of the solvent.

The starting materials of formula II are known or can be prepared in an analogous manner to the preparation of the known compounds. The following reaction schemes illustrate the preparation of these formula II compounds.

Scheme I

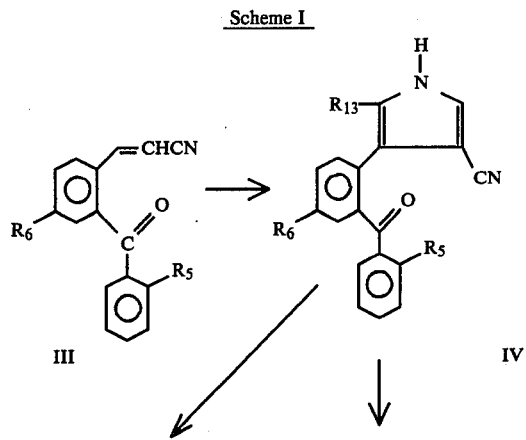

-continued
Scheme I

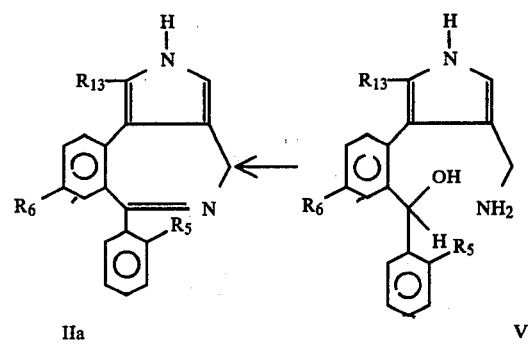

wherein $R_{13}$ is hydrogen or lower alkyl and $R_5$ and $R_6$ are as above.

III→IV

The compound of formula III can be reacted with an α-tosyl alkylisocyanide in the presence of a base such as sodium hydride using a mixture of dimethylsulfoxide and an ether, such as diethylether, dioxane or tetrahydrofuran as solvent. The reaction temperatures may range from about 0° C. to about 40° C., with about room temperature being preferred. The α-tosyl alkylisocyanides mentioned above may be prepared following the teaching of van Leusen et al., Tetrahedron Letters, 3487(1975).

IV→IIa

The compound of formula IV can be reacted with hydrogen at pressures ranging from about atmospheric pressure to five atmospheres in the presence of a transition metal catalyst, such as Raney nickel using glacial acetic acid as solvent. The resulting amine thus formed cyclizes spontaneously to the azepine ring. The reaction temperature is suitably about room temperature.

The first formed ring open amine is not isolated but is allowed to cyclize in situ to product IIa.

IV→V

The compound of formula IV can be reacted with a metal hydride reducing agent, such as lithium aluminum hydride in an etherial solvent such as tetrahydrofuran. The reaction temperature may range from about −20° C. to about room temperature, with about 0° C. being preferred.

V→IIa

The compound of formula V can be reacted with manganese dioxide in an ether solvent, such as tetrahydrofuran or another suitable solvent, such as toluene. The resulting amine thus formed cyclizes spontaneously to the azepine ring. The reaction temperature may range from about room temperature to the boiling point of the solvent, with about 40° C. being preferred.

Scheme II

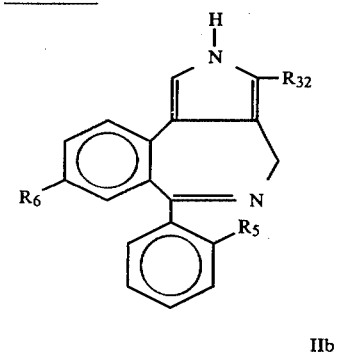

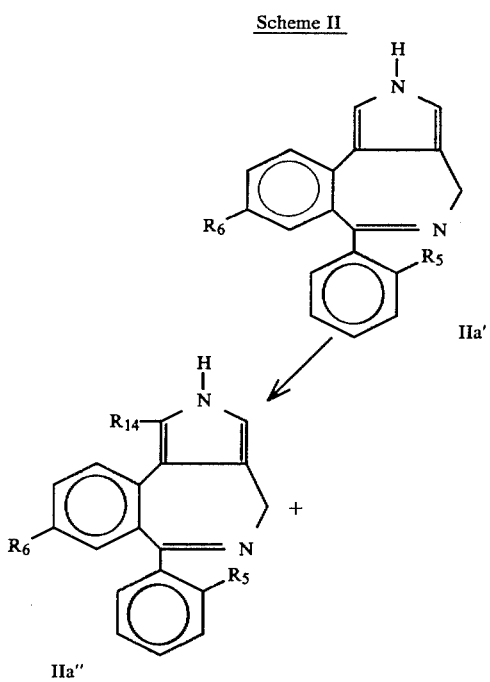

wherein $R_{14}$ and $R_{32}$ are lower alkyl and $R_5$ and $R_6$ are as above.

$$IIa' \rightarrow IIa'' + IIb$$

The compound of formula IIa' can be reacted with one equivalent of a strong base such as lithium diisopropylamide at between about $-80°$ C. to about $0°$ C., with about $-20°$ C. being preferred. The resulting anion is treated with the desired alkylating agent, such as a lower alkyl halide or sulfonate. A mixture of formula IIa'' and IIb isomers results which can be separated by standard column chromatography procedures.

Scheme III

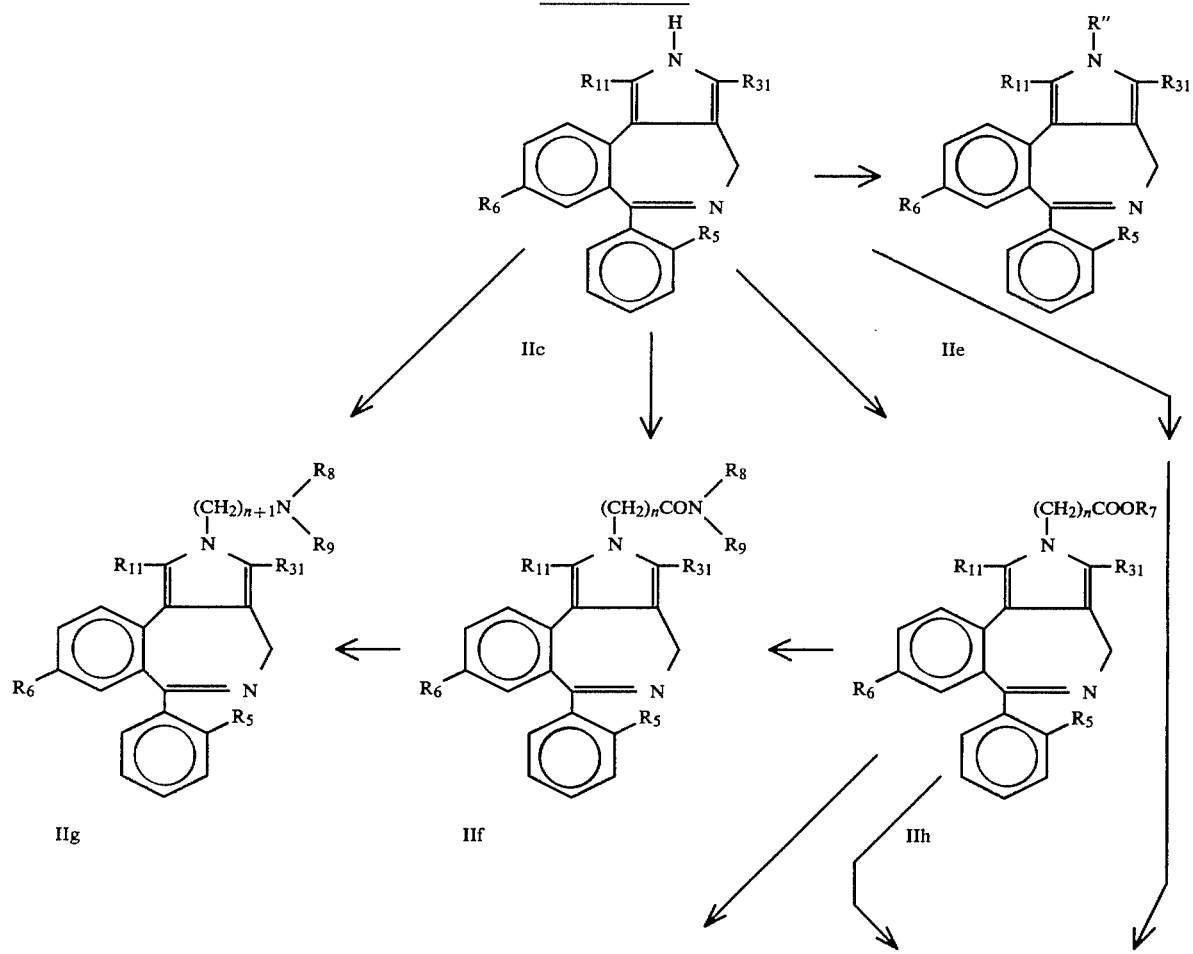

-continued
Scheme III

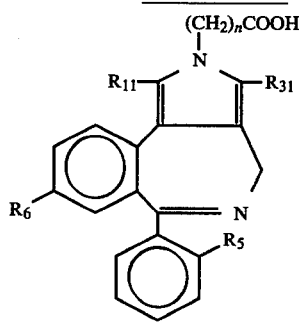

IIj

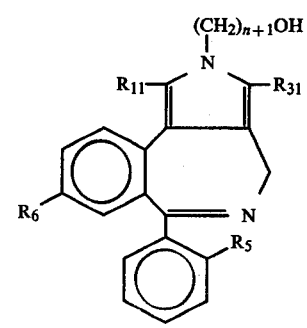

IIi wherein R" is lower alkyl, $R_7$ is lower alkyl, $R_8$ and $R_9$ are hydrogen or lower alkyl and n is an integer from 1 to 6 and $R_{11}$, $R_{31}$, $R_5$ and $R_6$ are as above.

IIc→IIh→IIj

A compound of the formula IIc can be reacted with a halo ester such as ethyl bromoacetate or ethyl 3-bromopropionate in the presence of a base such as an alkali metal alkoxide in a polar solvent such as dimethyl sulfoxide or dimethylformamide. The reaction temperature may range from about $-20°$ C. to about room temperature, with about $0°$ C. being preferred. If desired, the product of formula IIh thus obtained may be treated with an alkali metal carbonate or hydroxide in an aqueous ethereal solvent, such as tetrahydrofuran. Subsequent addition of a strong mineral acid thus yields the corresponding carboxylic acid of formula IIj.

IIh→IIf

A compound of the formula IIh can be reacted with ammonia or a mono- or di-substituted lower alkyl amine and a catalytic amount of its hydrochloride salt with a $C_1$ to $C_4$ alcohol solvent. The reaction is usually conducted at about $100°$ C. using a pressure apparatus to contain the volatile reactants.

IIh→IIi

A compound of the formula IIh can be reacted with a metal hydride such as lithium aluminum hydride in an ethereal solvent such as tetrahydrofuran or dioxane. The reaction temperature may range from about $-80°$ C. to about room temperature, with about $0°$ C. being preferred.

IIc→IIg

A compound of the formula IIc can be reacted with a compound of the formula

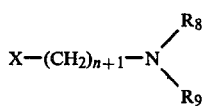   V wherein X is halide or sulfonate and $R_8$, $R_9$ and n are as above in the presence of a base such as an alkali metal alkoxide in a polar solvent such as dimethyl sulfoxide or dimethylformamide. The reaction temperature may range from about $-20°$ C. to about room temperature with about room temperature being preferred.

IIc→IIe

A compound of the formula IIc can be reacted with a base such as an alkali metal alkoxide, e.g., potassium or sodium methoxide, followed by an alkylating agent, such as a lower alkyl, halide or sulfonate in a polar aprotic solvent such as dimethylformamide or dimethyl sulfoxide. The reaction temperature may range from about $0°$ C. to about room temperature, with about $0°$ C. being preferred.

IIf→IIg or IIh→IIi

A compound of the formula IIf or IIh is reacted with a metal hydride reducing agent, such as lithium aluminum hydride in an ether solvent, such as tetrahydrofuran. The reaction temperature may range from about $-20°$ C. to about room temperature, with about $0°$ C. being preferred.

IIc→IIi

A compound of formula IIc can be reacted in the presence of a base such as an alkali metal alkoxide, and dimethylformamide or dimethyl sulfoxide with a compound of the formula $$X\text{—}(CH_2)_{n+1}OZ \qquad VI$$

wherein Z is a hydroxy protecting group and X and n are as above.

Suitable hydroxy protecting groups include the tetrahydropranyl ether group. Subsequent treatment with aqueous acid yields the desired end product.

IIc→IIf

A compound of formula IIc can be reacted with a compound of the formula

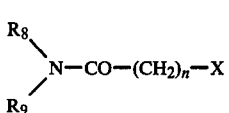   IV wherein X is as above and $R_8$, $R_9$ and n are as above in the presence of a base such as an alkali metal alkoxide, and dimethylformamide or dimethyl sulfoxide.

The pyrrolo[3,4-d][2]benzazepinones above are useful as pharmaceuticals and are characterized by activity as sedatives and anxiolytic agents. These compounds can be used in the form of conventional pharmaceutical preparations; for example, the aforesaid compounds can be mixed with conventional organic or inorganic, inert pharmaceutical carriers suitable for parenteral or enteral administration such as, for example, water, gelatin, lactose, starch, magnesium stearate, talc, vegetable oil, gums, polyalkylene glycols, Vaseline or the like. They can be administered in conventional pharmaceutical forms, e.g., solid forms, for example, tablets, dragees, capsules, suppositories or the like, or in liquid forms, for example, solutions, suspensions or emulsions. Moreover, the pharmaceutical compositions containing compounds of this invention can be subjected to conventional pharmaceutical expedients such as sterilization, and can contain conventional pharmaceutical excipients such as preservatives, stabilizing agents, wetting agents, emulsifying agents, salts for the adjustment of osmotic pressure, or buffers. The compositions can also contain other therapeutically active materials.

A suitable pharmaceutical dosage unit can contain from about 0.1 to about 500 mg of the benzazepinone end products with a dosage range of from about 0.1 mg to about 100 mg being the preferred oral administration and a dosage range of from about 0.1 mg to about 50 mg being preferred for parenteral administration. However, for any particular subject, the specific dosage regimen should be adjusted according to individual need and the professional judgement of the person administering or supervising the administration of the aforesaid compounds. It is to be understood that the dosages set forth herein are exemplary only and that they do not, to any extent, limit the scope or practice of this invention.

The term "dosage unit" as employed throughout this specification refers to pharmaceutically discrete units suitable as unitary dosages for mammalian subject each containing a predetermined quantity of active material calculated to produce the desired therapeutic effect in association with the required pharmaceutical diluent, carrier or vehicle.

The following data is indicative of the pharmacological activities of the pyrrolo-benzazepinones utilizing pharmacological tests well-known in the art.

$^3$H-Diazepam Binding Assay

Brief-Description: Rat brain cortical fragments are prepared and the binding procedures performed as described by Mohler and Okada (Life Sciences, 20, 2101, 1977) except that Tris buffer is substituted for Krebs buffer. Drugs are assayed in triplicate.

Measurements Made: Radioactivity is measured by liquid scintillation counting.

Results Expressed As: $IC_{50}$ (nM), concentration required to inhibit binding by 50%.

Activity of Standard Drugs:

| Drug | $IC_{50}$ (nM) |
|---|---|
| Diazepam | 5.0 |
| Flunitrazepam | 1.8 |
| Flurazepam | 15.6 |

The Assay acts as a screen for antianxiety drugs.
Results:

| Compound | $IC_{50}$ (nM) |
|---|---|
| 8-chloro-6-(2-chlorophenyl)-1,4-dihydro-2-methylpyrrolo[3,4-d][2]benzazepin-3(2H)—one $LD_{50}$ - 800 mg/kg (po) (mice) | 0.006 |
| 8-chloro-6-(2-chlorophenyl)-1,4-dihydro-1-methylpyrrolo[3,4-d][2]benzazepin-3(2H)—one $LD_{50}$ - greater than 1000 mg/kg (po) (mice) | 1.0 |

-continued

| Compound | $IC_{50}$ (nM) |
|---|---|
| 8-chloro-6-(2-chlorophenyl)-1,4-dihydropyrrolo[3,4-d][2]benzazepin-3(2H)—one 0.25 molar hydrate micronized $LD_{50}$ - greater than 1000 mg/kg (po) (mice) | 0.003 |
| 8-chloro-6-(2-chlorophenyl)-1,4-dihydropyrrolo[3,4-d][2]benzazepin-3(2H)—one $LD_{50}$ - 300 mg/kg (po) (mice) | 0.002 |

Intravenous Antimetrazol Test

Brief Description: Male CF-1 mice, 45–54 days old, housed in facilities for one week and food-deprived for about 24 hours, are used in this test. The test compound, dispersed in 5% acacia, is administered orally to three mice at 1/10 the dose at which lethality occurred in the TSP testing. One hour later, metrazol is administered intravenously at 70 mg/kg (convulsant dose 100 mg/kg) and animals are observed 30 seconds for protection against convulsions. If the compound is active orally, 3 animals are used per dose level. The dose at which 50% of the animals are protected from convulsive seizures is expressed as the $ED_{50}$.

Measurements Made: The number of animals protected from convulsions.

Calculations: If the drug is active and three mice are used per dose level, the approximate $ED_{50}$ is calculated by the method of Miller and Tainter (Proc. Soc. Exp. Biol. Med. 57:261, 1944). If six or more mice are used per dose level, the $ED_{50}$ values and 95% fiducial limits are calculated using a computer program based on the method of D. J. Finney ("Probit Analysis", Cambridge University Press, Cambridge, England, 1971).

Activity of Standard Drugs:

| Drug | $ED_{50}$ (95% Fiducial Limits) mg/kg po |
|---|---|
| Chlordiazepoxide | 3.9 |
| Diazepam | 1.0 |
| Sodium Phenobarbital | 19 |

The test evaluates anticonvulsant agents and is considered to be predictive of anxiolytic activities.
Results:

| Compound | $ED_{50}$ mg/kg po |
|---|---|
| 8-chloro-6-(2-chlorophenyl)-1,4-dihydro-2-methylpyrrolo[3,4-d][2]benzazepin-3(2H)—one $LD_{50}$ - 800 mg/kg (po) | 0.08 |
| 8-chloro-6-(2-chlorophenyl)-1,4-dihydro-1-methylpyrrolo[3,4-d][2]benzazepin-3(2H)—one $LD_{50}$ - greater than 1000 mg/kg (po) | 0.08 |
| 8-chloro-6-(2-chlorophenyl)-1,4-dihydropyrrolo[3,4-d][2]benzazepin-3(2H)—one 0.25 molar hydrate micronized $LD_{50}$ - greater than 1000 mg/kg (po) | 0.07 |
| 8-chloro-6-(2-chlorophenyl)-1,4-dihydropyrrolo[3,4-d][2]benzazepin-3(2H)—one $LD_{50}$ - 300 mg/kg (po) | 0.03 |

The following examples are illustrative of the invention but are not meant to limit such invention.

EXAMPLE 1

2-Benzyl-4-chlorobenzoic acid

To a solution of 5.0 g of cupric sulfate in 3 liters of concentrated ammonium hydroxide solution were added 300 g (4.6 mol) of activated zinc dust and 100 g (0.42 mol) of 2-benzoyl-4-chlorobenzoic acid. The mixture was refluxed for 3 days, during which the volume was maintained by the addition of concentrated ammonium hydroxide solution. The mixture was cooled, and the excess zinc was removed by filtration. The filtrate was acidified by the addition of concentrated hydrochloric acid to a pH of 3. The resulting precipitate was collected by filtration and dried to constant weight to give a white solid, mp 142°–144° C.

EXAMPLE 2

2-Benzyl-4-chlorobenzyl alcohol

To a solution of 28.4 g (0.75 mol) of lithium aluminum hydride in 800 ml of ether, which was cooled to 0° C., were added dropwise 85.1 g (0.345 mmol) of 2-benzyl-4-chlorobenzoic acid in 250 ml of ether. The mixture was allowed to warm to room temperature and was stirred for 2 hours. The excess lithium aluminum hydride was discharged by the addition of 28.5 ml of water, 28.5 ml of 10% aqueous sodium hydroxide solution, and 85.5 ml of water. The precipitate was removed by filtration, and the filtrate was dried over sodium sulfate. Removal of the ether at reduced pressure gave a colorless oil which crystallized upon standing, mp 46.5°–49° C.

EXAMPLE 3

2-Benzyl-4-chlorobenzaldehyde

To a suspension of 238 g (1.1 mol) of pyridinium chlorochromate and 300 ml of methylene chloride were added 79.3 g (0.34 mol) of 2-benzyl-4-chlorobenzyl alcohol. The mixture was stirred at room temperature for 2 hours. The chromium salts were precipitated by the addition of 2.4 liters of a 1:1 mixture of ether and petroleum ether, and the precipitate was removed by filtration through Celite. The solvent was removed at reduced pressure to give a yellow oil, which was used without further purification.

EXAMPLE 4

3-[2-Benzyl-4-chlorophenyl]-2-propenenitrile

To a suspension of 10.5 g (0.437 mol) of mineral oil free sodium hydride in 1.2 liters of tetrahydrofuran were added dropwise 58.4 g (0.328 mol) of diethylcyanomethyl phosphonate. After the hydrogen evolution had ceased (ca 60 min.), 69.4 g (0.3 mol) of 2-benzyl-4-chlorobenzaldehyde, in 75 ml of tetrahydrofuran, were added dropwise. The mixture was stirred overnight at room temperature. The tetrahydrofuran solution was decanted and concentrated at room temperature. The residue was partitioned between 2 liters of water and 1.5 liters of ether. The ether solution was separated, washed with water, and dried over sodium sulfate. The ether was removed at reduced pressure to give a yellow oil which was used without further purification.

EXAMPLE 5

3-(2-Benzoyl-4-chlorophenyl)-2-propenenitrile

A mixture of 28.8 g (0.14 mol) of 3-[2-benzyl-4-chlorophenyl]-2-propenenitrile, 50 g (0.5 mol) of chromium trioxide, 100 ml of methylene chloride, and 300 ml of acetic acid was stirred at room temperature overnight. The excess chromium trioxide was discharged by the slow addition of 30 ml of ethanol. The mixture was diluted with 800 ml of water and extracted with 500 ml of ether. The ether solution was washed with water, saturated aqueous sodium bicarbonate, and saturated aqueous sodium chloride. The ether solution was dried over anhydrous sodium sulfate and concentrated at reduced pressure to give a yellow oil which was used without further purification.

A sample of the product was purified by preparative layer chromatography (silica gel, 2 mm; 1:1 mixture of methylene chloride and pentane) to give a white solid, mp 87°–89° C.

EXAMPLE 6

4-[2-Benzoyl-4-chlorophenyl]-1H-pyrrole-3-carbonitrile

A mixture of 10.7 g (40 mmol) of 3-(2-benzoyl-4-chlorophenyl)-2-propenenitrile, 5.3 g (38 mmol) of tosylmethyl isocyanide, 75 ml of dimethyl sulfoxide and 150 ml of ether were added dropwise to a suspension of 3.7 g (77 mmol) of 50% sodium hydride in mineral oil and 170 ml of ether. When the addition was complete, stirring was continued for 2 hours. The mixture was diluted with water, and the ether layer was separated. The aqueous solution was extracted with ether. The combined ether extracts were washed with water, dried over anhydrous sodium sulfate and concentrated at reduced pressure to give a dark green oil. Purification by column chromatography (800 g silica gel; eluent, 5% ether in methylene chloride) gave end product as off-white prisms, mp 175°–177° C.

EXAMPLE 7

8-Chloro-6-phenyl-2H,4H-pyrrolo[3,4-d][2]benzazepine

A mixture of 4.0 g (13 mmol) of 4-[2-benzoyl-4-chlorophenyl]-1H-pyrrole-3-carbonitrile, 4 g of Raney nickel, and 300 ml of acetic acid were hydrogenated on a Parr apparatus for 4 hours. The Raney nickel was removed by filtration, and the filtrate was diluted with 400 ml of ice water. The acetic acid was neutralized with sodium bicarbonate, and the resulting solution extracted with methyene chloride. The methylene chloride solution was washed with water and dried over sodium sulfate. Concentration of the methylene chloride solution gave a yellow solid. Recrystallization from methylene chloride/ether gave end product as white solid, mp 203°–206° C.

EXAMPLE 8

8-Chloro-1,4-dihydro-6-phenylpyrrolo[3,4-d][2]benzazepin-3(2H)-one

In one portion, 4.0 g (13.6 mmol) of 8-chloro-6-phenyl-2H,4H-pyrrolo[3,4-d][2]benzazepine were added to a mixture of 3.4 g (15.7 mmol) of m-chlorperbenzoic acid in 100 ml of 2% concentrated sulfuric acid in acetic acid and the resulting mixture was stirred for 1 hour. The excess peracid was discharged by the addition of saturated aqueous sodium bisulfide solution, and the mixture was concentrated at reduced pressure. The residue was partitioned between methylene chloride and water and neutralized with concentrated ammonium hydroxide solution. The methylene chloride solution was washed with brine, dried over anhydrous sodium sulfate and concentrated at reduced pressure to a dark residue. Purification of the residue by column chromatography (silica gel, 100 g; eluent 5% methanol in methylene chloride) gave after crystallization from ethyl acetate end product as pale yellow prisms, mp 205°–208° C.

Thin layer chromatography of the crystallization filtrates indicated the presence of the isomeric 8-chloro-3,4-dihydro-6-phenylpyrrolo[3,4-d][2]benzazepin-1(2H)-one.

EXAMPLE 9

α,4-Dichloro-2-(benzoyl)benzenepropanenitrile

A solution of 92.7 g (0.4 mol) of 2-amino-5-chlorobenzephenone in 250 ml of acetonitrile was added to a mixture of 70 g (0.52 mol) of cupric chloride, 65 g (0.63 mole) of t-butylnitrite, 500 ml of acrylonitrile and 500 ml of acetonitrile. When the addition was complete, stirring at room temperature was continued for 2 hours. The mixture was diluted with 80 ml of 6 N hydrochloric acid and 1500 ml of water, extracted with ether and dried over anhydrous sodium sulfate. The ether solution was concentrated at reduced pressure to give a brown oil, which contained the end product and 2,5-dichlorobenzophenone. Trituration of the oil with a mixture of ether and petroleum ether gave the end product as a tan solid. Recrystallization of a small portion of the end product from a mixture of ether and petroleum ether gave pale yellow needles, mp 69°–71° C.

EXAMPLE 10

α,4-Dichloro-2-(2-fluorobenzoyl)benzenepropanenitrile

The preparation of α,4-dichloro-2-(2-fluorobenzoyl)benzenepropanenitrile was conducted in the same manner as the preparation of α,4-dichloro-2-(benzoyl)benzenepropanenitrile described in Example 9 to give pale yellow prisms, mp 94°–95° C.

EXAMPLE 11

α,4-Dichloro-2-(2-chlorobenzoyl)benzenepropanenitrile

The preparation of α,4-dichloro-2-(2-chlorobenzoyl)benzenepropanenitrile was conducted in the same manner as the preparation of α,4-dichloro-2-(benzoyl)benzenepropanenitrile described in Example 9 to give off-white prisms, mp 102°–103° C.

EXAMPLE 12

3-(2-Benzoyl-4-chlorophenyl)-2-propenenitrile

A mixture of 50.9 g (0.168 mol) of α,4-dichloro-2-(benzoyl)benzenepropanenitrile, 17 g (0.14 mol) of potassium carbonate, 50.9 g (0.5 mol) of potassium bicarbonate and 510 ml of dimethyl sulfoxide was stirred at room temperature for 48 hours. The mixture was diluted with 1.5 liters of water, and the resulting precipitate was collected by filtration. Recrystallization from a mixture of methylene chloride and ether gave off-white prisms, mp 89°–91° C.

EXAMPLE 13

3-[2-(2-Fluorobenzoyl)-4-chlorophenyl]-2-propenenitrile

The preparation of 3-[2-(2-fluorobenzoyl)-4-chlorophenyl]-2-propenenitrile was conducted in the same manner as the preparation of 3-(2-benzoyl-4-chlorophenyl)-2-propenenitrile described in Example 12 to give off-white prisms, mp 137°–139° C.

EXAMPLE 14

3-[2-(2-Chlorobenzoyl)-4-chlorophenyl]-2-propenenitrile

The preparation of 3-[2-(2-chlorobenzoyl)-4-chlorophenyl]-2-propenenitrile was conducted in the same manner as the preparation of 3-(2-benzoyl-4-chlorophenyl)-2-propenenitrile described in Example 12 to give off-white prisms, mp 140°–141° C.

EXAMPLE 15

3-[2-(2-Fluorobenzoyl)-4-chlorophenyl]-2-propenenitrile

A solution of 5.0 g (14 mmol) of 5-chloro-2'-fluoro-2-iodobenzophenone, 2 ml (14.3 mmol) of triethylamine, 2 ml (30 mmol) of acrylonitrile and 35 mg (1.5 mmol) of palladium acetate was refluxed under an atomsphere of argon for 16 hours. The mixture was diluted with 100 ml of 1 N hydrochloric acid and the resulting precipitate was collected by filtration. The precipitate was washed with ether and air dried to give an off-white solid, mp 130°–133° C.

EXAMPLE 16

4-[2-(2-Fluorobenzoyl)-4-chlorophenyl]-1H-pyrrole-3-carbonitrile

The preparation of 4-[2-(2-fluorobenzoyl)-4-chlorophenyl]-1H-pyrrole-3-carbonitrile was conducted in the same manner as the preparation of 4-[2-benzoyl-4-chlorophenyl]-1H-pyrrole-3-carbonitrile described in Example 6 to give off-white prisms, mp 177°–179° C.

EXAMPLE 17

8-Chloro-6-(2-fluorophenyl)-2H,4H-pyrrolo[3,4-d][2]benzazepine

A mixture of 3.0 g (9 mmol) of 4-[2-(2-fluorobenzoyl)-4-chlorophenyl]-1H-pyrrole-3-carbonitrile, ca 3 g of Raney nickel and 150 ml of glacial acetic acid was hydrogenated on a Parr apparatus at 50 psi for 6 hours. The Raney nickel was removed by filtration, and the acetic acid was removed at reduced pressure to give a yellow oil. The yellow oil was poured on to ice, basified with ammonium hydroxide solution and extracted with methylene chloride. The methylene chloride solution was dried over anhydrous sodium sulfate and concentrated at reduced pressure to give tan crystals. Recrystallization from a mixture of ether and methylene chloride gave cream-colored prisms, mp 197°–199° C.

EXAMPLE 18

8-Chloro-6-(2-fluorophenyl)-3,4-dihydropyrrolo[3,4-d][2]benzazepin-1(2H)-one and
8-chloro-6-(2-fluorophenyl)-1,4-dihydropyrrolo[3,4-d][2]benzazepin-3(2H)-one In one portion, 5.0 ml (42.1 mmol) of 30% hydrogen peroxide solution was added to 100 ml of a 1% solution of concentrated sulfuric acid in acetic acid. After stirring for 1 hour, 5.0 g (16.0 mmol) of 8-chloro-6-(2-fluorophenyl)-2H,4H-pyrrolo[3,4-d][2]benzazepine were added, and the resulting mixture was stirred for 4 hours, The excess peracid was discharged by the addition of saturated aqueous sodium bisulfite solution, and the mixture was concentrated at reduced pressure. The residue was partitioned between methylene chloride and water and basified with concentrated ammonium hydroxide solution. The methylene chloride solution was washed with brine, dried over anhydrous sodium sulfate and concentrated at reduced pressure to give 5.0 g of a residue. Purification by HPLC (silical gel; eluent, 3% methanol in methylene chloride) gave in the first product band after crystallization from ethyl acetate 8-chloro-6-(2-fluorophenyl)-3,4-dihydropyrrolo[3,4-d][2]benzazepin-1(2H)-one as pale yellow prisms, mp 223°–225° C.

Further elution gave in the second product band after crystallization from ethyl acetate 8-chloro-6-(2-fluorophenyl)-1,4-dihydropyrrolo[3,4-d][2]benzazepin-3(2H)-one as colorless prisms, mp 217°–218° C.

EXAMPLE 19

4-[2-(2-Chlorobenzoyl)-4-chlorophenyl]-1H-pyrrole-3-carbonitrile

The preparation of 4-[2-(2-chlorobenzoyl)-4-chlorophenyl]-1H-pyrrole-3-carbonitrile was conducted in the same manner as the preparation of 4-[2-benzoyl-4-chlorophenyl]-1H-pyrrole-3-carbonitrile described in Example 6 to give off-white prisms, mp 182°–184° C.

EXAMPLE 20

8-Chloro-6-(2-chlorophenyl)-2H,4H-pyrrolo[3,4-d][2]benzazepine

The preparation of 8-chloro-6-(2-chlorophenyl)-2H,4H-pyrrolo[3,4-d][2]benzazepine was conducted in the same manner as the preparation of 8-chloro-6-(2-fluorophenyl)-2H,4H-pyrrolo[3,4-d][2]benzazepine described in Example 17 to give cream-colored prisms, mp 204°–206° C.

EXAMPLE 21

8-Chloro-6-(2-chlorophenyl)-1,4-dihydropyrrolo[3,4-d][2]benzazepin-3(2H)-one and
8-chloro-6-(2-chlorophenyl)-3,4-dihydropyrrolo[3,4-d][2]benzazepin-1(2H)-one In one portion, 10.0 g (30.5 mmol) of 8-chloro-6-(2-chlorophenyl)-2H,4H-pyrrolo[3,4-d][2]benzazepine were added to a mixture of 7.6 g (35.2 mmol) of 80% m-chloroperbenzoic acid in 225 ml of 2% concentrated sulfuric acid in acetic acid and stirred at room temperature for 1 hour. The excess peracid was discharged with saturated aqueous sodium bisulfite solution, and the mixture was concentrated at reduced pressure. The residue was partitioned between methylene chloride and water and basified with concentrated ammonium hydroxide solution. The methylene chloride solution was washed with brine, dried over anhydrous sodium sulfate, and concentrated at reduced pressure to give 10.0 g of a yellow residue. Crystallization from methylene chloride gave 8-chloro-6-(2-chlorophenyl)-1,4-dihydropyrrolo[3,4-d][2]benzazepin-3(2H)-one as pale yellow prisms, mp 243°–244° C. Crystallization of the mother liquor from ethyl acetate gave 8-chloro-6-(2-chlorophenyl)-3,4-dihydropyrrolo[3,4-d][2]benzazepin-1(2H)-one as pale yellow prisms, mp 195°–197° C.

EXAMPLE 22

8-chloro-6-(2-chlorophenyl)-3,4-dihydropyrrolo[3,4-d][2]benzazepin-1(2H)-one and
8-chloro-6-(2-chlorophenyl)-1,4-dihydropyrrolo[3,4-d][2]benzazepin-3(2H)-one In one portion, 9.8 ml of 30% hydrogen peroxide solution were added to 195 ml of a 1% solution of concentrated sulfuric acid in acetic acid. The mixture was stirred at room temperature for 1 hour. In one portion, 9.8 g (30 mmol) of 8-chloro-6-(2-chlorophenyl)-2H,4H-pyrrolo[3,4-d][2]benzazepine were added to the mixture and stirred at room temperature for 2.5 hours. The excess peracid was discharged by the addition of saturated aqueous sodium bisulfite solution, and the mixture was concentrated at reduced pressure. The residue was partitioned between methylene chloride and water and basified with concentrated ammonium hydroxide solution. The methylene chloride solution was washed with brine, dried over anhydrous sodium sulfate, and concentrated at reduced pressure to give 10.0 g of a yellow residue. Purification of the residue by column chromatography (silica gel, 200 g; eluent, 5% methanol in methylene chloride) gave in the first product band after crystallization from ethyl acetate 8-chloro-6-(2-chlorophenyl)-3,4-dihydropyrrolo[3,4-d][2]benzazepin-1(2H)-one as pale yellow prisms, mp 195°–197° C. Further elution gave in the second product band after crystallization from methylene chloride 8-chloro-6-(2-chlorophenyl)-1,4-dihydropyrrolo[3,4-d][2]benzazepin-3(2H)-one as colorless prisms, mp 243°–244° C.

EXAMPLE 23

8-Chloro-6-(2-chlorophenyl)-3,4-dihydropyrrolo[3,4-d][2]benzazepin-1(2H)-one-5-oxide and
8-chloro-6-(2-chlorophenyl)-1,4-dihydropyrrolo[3,4-d][2]benzazepin-3(2H)-one-5-oxide In one portion, 15.0 g (69.5 mmol) of 80% m-chloroperbenzoic acid were added to a solution of 10.0 g (30.5 mmol) of 8-chloro-6-(2-chlorophenyl)-2H,4H-pyrrolo[3,4-d][2]benzazepine in 350 ml of methylene chloride which was cooled to 0° C. The reaction mixture was stirred at 0° C. for 2.5 hours and then neutralized with saturated aqueous sodium bicarbonate solution. The methylene chloride solution was washed with water, dried over anhydrous sodium sulfate and concentrated at reduced pressure to yield 11.0 g of a yellow residue. Purification of the residue by column chromatography (silica gel, 150 g; eluent, 5% methanol in methylene chloride) gave a mixture of the two end products. Further purification of the mixture by chromatography (alumina, 150 g; eluent, 5% methanol in methylene chloride) gave in the first product band after crystallization from a mixture of ethyl acetate and methanol 8-chloro-6-(2-chlorophenyl)-3,4-dihydropyrrolo[3,4-d][2]benzazepin-1(2H)-one-5-oxide as pale yellow prisms, mp 243°–244° C.

Further elution gave in the second product band after crystallization from a mixture of ethyl acetate and methanol 8-chloro-6-(2-chlorophenyl)-1,4-dihydropyrrolo[3,4-d][2]benzazepin-3(2H)-one-5-oxide as pale yellow prisms solvated with 0.5 mole of methanol, mp 234°–236° C.

EXAMPLE 24

8-Chloro-6-(2-chlorophenyl)-1,4-dihydropyrrolo[3,4-d][2]benzazepin-3(2H)-one

In one portion, 1.8 ml (20 mmol) of phosphorous trichloride were added to a solution of 0.9 g (2.5 mmol) of 8-chloro-6-(2-chlorophenyl)-1,4-dihydropyrrolo[3,4-d][2]benzazepin-3(2H)-one-5-oxide in 180 ml of methylene chloride. The mixture was refluxed for 1 hour and then concentrated at reduced pressure. The residue was dissolved in methylene chloride and neutralized with saturated aqueous sodium bicarbonate solution. The methylene chloride solution was dried over anhydrous sodium sulfate and concentrated at reduced pressure to give an orange solid. Recrystallization from ethyl acetate gave pale yellow prisms of a 0.25 mole hydrate, mp 255°–256° C.

EXAMPLE 25

8-Chloro-6-(2-chlorophenyl)-3,4-dihydropyrrolo[3,4-d][2]benzazepin-1(2H)-one

In one portion, 2 ml (2.3 mmol) of phosphorous trichloride were added to a solution of 1.0 g (2.7 mmol) of 8-chloro-6-(2-chlorophenyl)-3,4-dihydropyrrolo[3,4-d][2]benzazepine-1(2H)-one-5-oxide in 200 ml of methylene chloride and refluxed for 1 hour. The mixture was concentrated at reduced pressure. The residue was dissolved in methylene chloride and neutralized with saturated aqueous sodium bicarbonate solution. The methylene chloride solution was dried over anhydrous sodium sulfate and concentrated at reduced pressure to give a dark red residue. Purification of the residue by column chromatography (silica gel, 20 g; eluent, 5% methanol in methylene chloride) followed by crystallization from ethyl acetate gave 8-chloro-6-(2-chlorophenyl)-3,4-dihydropyrrolo[3,4-d][2]benzazepin-1(2H)-one as pale yellow prisms solvated with 0.5 mole ethyl acetate, mp 195°–197° C.

EXAMPLE 26

4-[4-Chloro-2-(2-chlorobenzoyl)phenyl]-5-methyl-1H-pyrrole-3-carbonitrile and
6-chloro-8-(2-chlorophenyl)-1,8-dihydro-8-hydroxy-2-methylindeno[2,1-b]pyrrole-3-carbonitrile A mixture of 33.9 g (0.11 mol) of 3-[2-(2-chlorobenzoyl)-4-chlorophenyl]-2-propenenitrile, 20 g (0.96 mol) of 1-tosylethyl isocyanide in 150 ml of dimethyl sulfoxide and 100 ml of ether was added dropwise to a suspension of 4.6 g (0.1 mol) of a 50% mineral oil dispension of sodium hydride in 100 ml of ether which was immersed in a room temperature water bath. Stirring at room temperature was continued for 2 hours. The mixture was diluted with 1.2 liters of water and 40 ml of 1 N hydrochloric acid and extracted with methylene chloride. The methylene chloride solution was washed with water, dried over anhydrous sodium sulfate and concentrated at reduced pressure to give a dark green oil. Crystallization from a mixture of ether and petroleum ether gave 4-[4-chloro-2-(2-chlorobenzoyl)phenyl]-5-methyl-1H-pyrrole-3-carbonitrile, mp 206°–208° C., as tan crystals. Recrystallization from ether gave the desired product as colorless crystals, mp 210°–211° C.

A second crop of crystals consisting of 6-chloro-8-(2-chlorophenyl)-1,8-dihydro-8-hydroxy-2-methylindeno[2,1-b]pyrrole-3-carbonitrile, mp 221°–225° C., was obtained from ether. Recrystallization from ether gave pale yellow prisms, melting at 232°–137° C.

EXAMPLE 27

8-Chloro-6-(2-chlorophenyl)-1-methyl-2H,4H-pyrrolo[3,4-d][2]benzazepine

A mixture of 8.5 g (24 mmol) of 4-[4-chloro-2-(2-chlorobenzoyl)phenyl]-5-methyl-1H-pyrrole-3-carbonitrile, 1 spoonful of Rancy nickel and 250 ml of glacial acetic acid was hydrogenated on a Parr apparatus at 55 psi overnight. The catalyst was removed by filtration, and the acetic acid was removed at reduced pressure. The residue was diluted with water, basified with concentrated ammonium hydroxide solution, and the resulting precipitate was collected by filtration. The precipitate was dissolved in tetrahydrofuran, dried over anhydrous sodium sulfate and concentrated at reduced pressure. The residue was crystallized from a mixture of ether and petroleum ether to give off-white crystals, mp 219°–222° C. Recrystallization from a mixture of ether and methylene chloride gave colorless crystals, mp 221°–225° C.

EXAMPLE 28

8-Chloro-6-(2-chlorophenyl)-1,4-dihydro-1-methylpyrrolo[3,4-d][2]benzazepin-3(2H)-one In one portion, 1 ml of 30% hydrogen peroxide was added to 40 ml of a 1% solution of concentrated sulfuric acid in acetic acid. After stirring for 1 hour, 2.0 g (5.8 mmol) of 8-chloro-6-(2-chlorophenyl)-1-methyl-2H,4H-pyrrolo[3,4-d][2]benzazepine were added, and the resulting mixture was stirred at room temperature for 30 minutes. The mixture was diluted with methylene chloride and neutralized with concentrated ammonium hydroxide solution. The methylene chloride solution was dried over anhydrous sodium sulfate and concentrated at reduced pressure to a dark residue. Crystallization from ethyl acetate gave 8-chloro-6-(2-chlorophenyl)-1,4-dihydro-1-methylpyrrolo[3,4-d][2]benzazepin-3(2H)-one as pale yellow prisms, mp 239°–241° C.

EXAMPLE 29

8-Chloro-6-(2-chlorophenyl)-2-methyl-2H,4H-pyrrolo[3,4-d][2]benzazepine

In one portion, 0.7 g (2.2 mmol) of 8-chloro-6-(2-chlorophenyl)-2H,4H-pyrrolo[3,4-d][2]benzazepine was added to a solution of 0.3 g (2.6 mmol) of potassium t-butoxide in 30 ml of dry dimethylformamide which was cooled to 0° C. After stirring for 15 minutes, 1.0 ml (16 mmol) of methyl iodide was added, and the mixture was allowed to warm to room temperature. Water was added, and the mixture was extracted with methylene chloride. The methylene chloride solution was washed with water, dried over anhydrous sodium sulfate, and concentrated at reduced pressure to give a yellow oil. Purification by column chromatography (silica gel, 20 g; eluent, 5% ether in methylene chloride) and recrystallization from a mixture of ether and petroleum ether gave colorless prisms, mp 167°–168° C.

The methanesulfonate salt of 8-chloro-6-(2-chlorophenyl)-2-methyl-2H,4H-pyrrolo[3,4-d][2]benzazepine was prepared by adding equimolar amounts of the base compound and methanesulfonic acid to methanol and isolated by precipitating the salt with the addition of ether. Recrystallization from a mixture of methanol and ether gave the methanesulfonate salt as orange prisms, mp 200°–203° C.

EXAMPLE 30

8-Chloro-6-(2-chlorophenyl)-3,4-dihydro-2-methylpyrrolo[3,4-d][2]benzazepin-1(2H)-one and 8-chloro-6-(2-chlorophenyl)-1,4-dihydro-2-methylpyrrolo[3,4-d][2]benzazepin-3(2H)-one In one portion, 1.4 ml of 30% hydrogen peroxide were added to 56 ml of a 1% solution of concentrated sulfuric acid in acetic acid. After stirring for 1 hour, 2.8 g (8.2 mmole) of 8-chloro-6-(2-chlorophenyl)-2-methyl-2H,4H-pyrrolo[3,4-d][2]benzazepine were added, and the resulting mixture was stirred at room temperature for 16 hours. The mixture was concentrated at reduced pressure and the residue was partitioned between methylene chloride and water. The methylene chloride solution was neutralized with concentrated ammonium hydroxide solution, washed with brine, dried over anhydrous sodium sulfate and concentrated at reduced pressure to a yellow residue. Purification of the residue by column chromatography (silica gel, 100 g; eluent, 5% methanol in methylene chloride) gave in the first product band after crystallization from ether 8-chloro-6-(2-chlorophenyl)-3,4-dihydro-2-methylpyrrolo-[3,4-d][2]benzazepin-1(2H)-one as yellow prisms, mp 177°–178° C.

Further elution gave in the second product band after crystallization from ether 8-chloro-6-(2-chlorophenyl)-1,4-dihydro-2-methylpyrrolo[3,4-d][2]benzazepin-3(2H)-one as pale yellow prisms, mp 173°–175° C.

EXAMPLE 31

4-[4-Chloro-2-(2-chlorophenyl)phenyl]-5-ethyl-1H-pyrrole-3-carbonitrile and 6-chloro-8-(2-chlorophenyl)-2-ethyl-1,8-dihydro-8-hydroxyindeno[2,1-b]pyrrole-3-carbonitrile A solution of 30.0 g (99.3 mmol) of 3-[2-(2-chlorobenzoyl)-4-chlorophenyl]-3-propenenitrile and 23.0 g (103 mmol) of 1-tosylpropyl isocyanide in a mixture of 200 ml of ether and 200 ml of dimethyl sulfoxide was added dropwise over a 20 minute period to an ice-cooled suspension of 6.7 g (140 mmol) of a 50% mineral oil dispersion of sodium hydride in 145 ml of ether. After stirring for 1.5 hours, 500 ml of water were added dropwise, followed by 50 ml of 1 N aqueous hydrochloric acid. The aqueous solution was extracted with 3×500 ml of ether. The ether solutions were combined and washed with 6×800 ml of water, dried over anhydrous sodium sulfate, and concentrated at reduced pressure to give 35.0 g of dark residue. Purification by column chromatography (silica gel, 500 g; eluent, 50% ether in petroleum ether) gave in the first product band after crystallization from a mixture of ether and methylene chloride 4-[4-chloro-2-(2-chlorophenyl)phenyl]-5-ethyl-1H-pyrrole-3-carbonitrile as off-white prisms, mp 163°–164° C.

Further elution gave in the second product band after crystallization from ether 6-chloro-8-(2-chlorophenyl)-2-ethyl-1,8-dihydro-8-hydroxyindeno[2,1-b]pyrrole-3-carbonitrile as colorless prisms, mp 172°–174° C.

EXAMPLE 32

8-Chloro-6-(2-chlorophenyl)-1-ethyl-2H,4H-pyrrolo[3,4-d][2]benzazepine

A mixture of 3.3 g (8.9 mmol) of 4-[2-(2-chlorobenzoyl)-4-chlorophenyl]-5-ethyl-1H-pyrrole-3-carbonitrile, 0.5 teaspoon of Raney nickel, and 100 ml of acetic acid was hydrogenated on a Parr apparatus at 50 psi for 16 hours. The Raney nickel was removed by filtration through a pad of Celite, and the filtrate was concentrated at reduced pressure to a dark residue. The residue was partitioned between ice water and ether and basified with concentrated ammonium hydroxide solution. The ether was removed at reduced pressure, and the aqueous residue was stirred for 1 hour. The resulting precipitate was collected by filtration and dissolved in tetrahydrofuran. The tetrahydrofuran solution was dried over anhydrous sodium sulfate and concentrated at reduced pressure to a residue which crystallized from ether to give 8-chloro-6-(2-chlorophenyl)-1-ethyl-2H,4H-pyrrolo[3,4-d][2]benzazepine as yellow prisms, mp 251°–253° C. Recrystallization from a mixture of ether and methylene chloride gave offwhite prisms, mp 254°–255° C.

EXAMPLE 33

8-Chloro-6-(2-chlorophenyl)-1-ethyl-1,4-dihydropyrrolo[3,4-d][2]benzazepin-3(2H)-one In one portion, 0.9 ml (7.9 mmol) of 30% hydrogen peroxide was added to 40 ml of a 1% solution of concentrated sulfuric acid in acetic acid. After stirring for 1 hour, 2.0 g (5.6 mmol) of 8-chloro-6-(2-chlorophenyl)-1-ethyl-2H,4H-pyrrolo[3,4-d][2]benzazepine were added, and the resulting mixture was stirred for 20 minutes. The excess peracid was discharged by the addition of saturated aqueous sodium bisulfite solution, and the mixture was concentrated at reduced pressure. The residue was partitioned between methylene chloride and water and neutralized with concentrated ammonium hydroxide solution. The methylene chloride solution was washed with brine, dried over anhydrous sodium sulfate, and concentrated at reduced pressure. The resulting oil was crystallized from ether to give 8-chloro-6-(2-chlorophenyl)-1-ethyl-1,4-dihydropyrrolo[3,4-d][2]benzazepin-3(2H)-one as yellow prisms, mp 233°–235° C. Recrystallization from a mixture of ethyl acetate and methanol gave colorless prims, mp 236°–237° C.

EXAMPLE 34

8-Chloro-6-(2-chlorophenyl)-1,2-dimethyl-2H,4H-pyrrolo[3,4-d][2]benzazepine

In one portion, 2.0 g (5.8 mmol) of 8-chloro-6-(2-chlorophenyl)-1-methyl-2H,4H-pyrrolo[3,4-d][2]benzazepine were added to an ice-cooled solution of 0.8 g (7.1 mmol) of potassium t-butoxide in 20 ml of dry dimethylformamide. After stirring at 0° C. for 10 minutes, 0.8 ml (12.8 mmol) of methyl iodide was added and the resulting solution was stirred for 20 minutes. The mixture was diluted with water, and the resulting precipitate was collected by filtration. The solid was dissolved in methylene chloride, dried over anhydrous sodium sulfate, and concentrated at reduced pressure to give 8-chloro-6-(2-chlorophenyl)-1,2-dimethyl-2H,4H-pyrrolo[3,4-d][2]benzazepine as orange prisms, mp 200°–202° C. A sample was recrystallized from a mixture of ether and methylene chloride to give pale yellow prisms, mp 203°–204° C.

EXAMPLE 35

8-Chloro-6-(2-chlorophenyl)-1,4-dihydro-1,2-dimethyl-pyrrolo[3,4-d][2]benzazepin-3(2H)-one In one portion, 0.7 ml (5.9 mmol) of a 30% hydrogen peroxide solution was added to 33 ml of a 1% solution of concentrated sulfuric acid in acetic acid. After stirring for 1 hour, 1.8 g (5.0 mmol) of 8-chloro-6-(2-chlorophenyl)-1,2-dimethyl-2H,4H-pyrrolo[3,4-d][2]benzazepine were added, and the resulting solution was stirred for 20 minutes. The excess peracid was discharged by the addition of saturated aqueous sodium bisulfite solution, and the mixture was concentrated at reduced pressure. The residue was partitioned between methylene chloride and water and basifified with concentrated ammonium hydroxide solution. The methylene chloride solution was washed with brine, dried over anhydrous sodium sulfate and concentrated at reduced pressure to a yellow residue. Crystallization from ethyl aceatate gave 8-chloro-6-(2-chlorophenyl)-1,4-dihydro-1,2-dimethylpyrrolo[3,4-d][2]benzazepin-3(2H)-one as pale yellow prisms, mp 207°–208° C.

EXAMPLE 36

8-Chloro-6-(2-chlorophenyl)-1-methyl-2H,4H-pyrrolo[3,4-d][2]benzazepine-2-acetic acid methyl ester In one portion, 2.0 g (5.8 mmol) of 8-chloro-6-(2-chlorophenyl)-1-methyl-2H,4H-pyrrolo[3,4-d][2]benzazepine were added to an ice-cooled solution of 0.8 g (7.1 mmol) of potassium t-butoxide in 30 ml of dry dimethylformamide. After stirring at 0° C. for 15 minutes, 0.65 ml (7.7 mmol) of methyl bromoacetate was added, and the resulting solution was stirred for 5 minutes. The mixture was diluted with water and extracted with ether. The ether solution was washed with water, dried over anhydrous sodium sulfate, and concentrated at reduced pressure to an oily residue. Purification of the residue by column chromatography (silica gel, 40 g; eluent, 5% ether in methylene chloride) gave after crystallization from a mixture of ether and petroleum ether 8-chloro-6-(2-chlorophenyl)-1-methyl-2H,4H-pyrrolo[3,4-d][2]benzazepine-2-acetic acid methyl ester as off-white prisms, mp 174°–176° C.

EXAMPLE 37

8-Chloro-6-(2-chlorophenyl)-1,4-dihydro-1-methyl-3-oxo-2H-pyrrolo[3,4-d][2]benzazepine-2-acetic acid methyl ester In one portion, 0.8 ml (7.0 mmol) of a 30% hydrogen peroxide solution was added to a solution of 35 ml of 1% concentrated sulfuric acid in acetic acid. After stirring the solution for 1 hour, 2.0 g (4.8 mmol) of 8-chloro-6-(2-chlorophenyl)-2H,4H-pyrrolo[3,4-d][2]benzazepine-2-acetic acid methyl ester were added, and the resulting solution was stirred for 30 minutes. The excess peracid was discharged with the addition of saturated aqueous sodium bisulfite solution, and the mixture was concentrated at reduced pressure. The residue was partitioned between methylene chloride and water and neutralized with concentrated ammonium hydroxide solution. The methylene chloride solution was washed with brine, dried over anhydrous sodium sulfate, and concentrated at reduced pressure to a residue which crystallized in ethyl acetate to give 8-chloro-6-(2-chlorophenyl)-1,4-dihydro-1-methyl-3-oxo-2H-pyrrolo[3,4-d][2]benzazepine-2-acetic acid methyl ester as pale yellow prisms, mp 221°–223° C. Recrystallization from ethyl acetate gave colorless prisms, mp 223°–224° C.

EXAMPLE 38

8-Chloro-6-(2-chlorophenyl)-1-methyl-2H,4H-pyrrolo[3,4-d][2]benzazepine-2-acetamide In one portion, 4.0 g (11.7 mmol) of 8-chloro-6-(2-chlorophenyl)-1-methyl-2H,4H-pyrrolo-[3,4-d][2]benzazepine were added to an ice-cooled solution of 1.6 g (14.2 mmol) of potassium t-butoxide in 60 ml of dry dimethylformamide. After stirring at 0° C. for 15 minutes, 1.4 g (15.0 mmol) of 2-chloroacetamide were added, and the resulting solution was stirred for 5 minutes. The mixture was diluted with water and extracted with methylene chloride. The methylene chloride solution was washed with water, dried over anhydrous sodium sulfate and concentrated at reduced pressure to a red residue. Purification of the residue by column chromatography (silica gel, 100 g; eluent, 50% ether in tetrahydrofuran) gave 8-chloro-6-(2-chlorophenyl)-1-methyl-2H,4H-pyrrolo[3,4-d][2]benzazepine-2-acetamide as a yellow solid. Recrystallization from ethyl acetate gave colorless needles, mp 142°–145° C.

EXAMPLE 39

8-Chloro-6-(2-chlorophenyl)-1,4-dihydro-1-methyl-3-oxo-2H-pyrrolo[3,4-d][2]benzazepine-2-acetamide In one portion, 0.7 ml (6.2 mmol) of 30% hydrogen peroxide was added to a 1% solution of concentrated sulfuric acid in acetic acid. After stirring for 1 hour, 1.7 g (4.2 mmol) of 8-chloro-6-(2-chlorophenyl)-1-methyl-2H,4H-pyrrolo[3,4-d][2]benzazepine-2-acetamide were added, and the resulting solution was stirred for 30 minutes. The excess peracid was discharged by the addition of saturated aqueous sodium bisulfite solution, and the mixture was concentrated at reduced pressure. The residue was partitioned between methylene chloride and water and neutralized with concentrated ammonium hydroxide solution. The methylene chloride solution was washed with brine, dried over anhydrous sodium sulfate, and concentrated at reduced pressure. The residue was crystallized from ethyl acetate to give 8-chloro-6-(2-chlorophenyl)-1,4-dihydro-1-methyl-3-oxo-2H-pyrrolo[3,4-d][2]benzazepine-2-acetamide as colorless prisms, mp 221°–222° C.

EXAMPLE 40

8-Chloro-6-(2-chlorophenyl)-1-methyl-2H,4H-pyrrolo[3,4-d][2]benzazepine-2-ethanol A solution of 4.0 g (9.6 mmol) of 8-chloro-6-(2-chlorophenyl)-1-methyl-2H,4H-pyrrolo[3,4-d][2]benzazepine-2-acetic acid methyl ester in 40 ml of tetrahydrofuran was added dropwise to a solution of 0.8 g (21.0 mmol) of lithuium aluminum hydride in 50 ml of tetrahydrofuran which was cooled to −78° C. When the addition was complete, the reaction mixture was allowed to warm to 0° C. and stirred for 30 minutes. The mixture was treated with 1 ml of water, 1 ml of a 3 N solution of aqueous sodium hydroxide and 3 ml of water. The resulting precipitate was removed by filtration, and the filtrate was concentrated at reduced pressure. The residue crystallized from ether to yield 8-chloro-6-(2-chlorophenyl)-1-methyl-2H,4H-pyrrolo[3,4-d][2]benzazepine-2-ethanol as pale yellow prisms, mp 149°–152° C. Recrystallization from a mixture of ether and methylene chloride gave white prisms, mp 151°–153° C.

EXAMPLE 41

2-[2-(Acetoxy)ethyl]-8-chloro-6-(2-chlorophenyl)-1,4-dihydro-1-methylpyrrolo[3,4-d][2]benzazepin-3(2H)-one and
8-chloro-6-(2-chlorophenyl)-1,4-dihydro-2-(2-hydroxyethyl)-1-methylpyrrolo[3,4-d][2]benzazepin-3(2H)-one In one portion, 0.58 ml (5.1 mmol) of 30% hydrogen peroxide was added to a 1% solution of concentrated sulfuric acid in acetic acid. After stirring for 1 hour, 1.3 g (3.3 mmol) of 8-chloro-6-(2-chlorophenyl)-1-methyl-2H,4H-pyrrolo[3,4-d][2]benzazepin-2-ethanol were added, and the resulting solution was stirred for 30 minutes. The excess peracid was discharged with the addition of saturated aqueous sodium bisulfite solution, and the mixture was concentrated at reduced pressure. The residue was partitioned between methylene chloride and water and neutralized with concentrated ammonium hydroxide solution. The methylene chloride solution was washed with brine, dried over anhydrous sodium sulfate, and concentrated at reduced pressure to a yellow residue. Purification by column chromatography (silica gel, 30 g; eluent, 3% methanol in methylene chloride) gave in the first product band after crystallization from a mixture of ether and methylene chloride 2-[2-(acetoxy)ethyl]-8-chloro-6-(2-chlorophenyl)-1,4-dihydro-1-methylpyrrolo[3,4-d][2]benzazepin-3(2H)-one as colorless prisms, mp 152°–154° C.

Further elution gave in the second product band after crystallization from a mixture of ethyl acetate and ether 8-chloro-6-(2-chlorophenyl)-1,4-dihydro-2-(2-hydroxyethyl)-1-methylpyrrolo[3,4-d][2]benzazepin-3(2H)-one as colorless prisms, mp 164°–165° C.

EXAMPLE 42

8-Chloro-6-(2-chlorophenyl)-3,4-dihydro-3-hydroxypyrrolo[3,4-d][2]benzazepin-1(2H)-one In one portion, 0.7 g (2 mmol) of 8-chloro-6-(2-chlorophenyl)-3,4-dihydropyrrolo[3,4-d][2]benzazepin-1(2H)-one was added to an ice-cooled solution of 2.6 g (15.8 mmol) of trichloroacetic acid and 2.0 g(4.4 mmol) of lead tetraacetate in 30 ml of methylene chloride. After stirring for 1 hour, the mixture was neutralized with saturated aqueous sodium bicarbonate solution. The methylene chloride solution was washed with water, dried over anhydrous sodium sulfate and concentrated at reduced pressure to a yellow residue. Purification of the residue by column chromatography (silica gel, 10 g; eluent, 5% methanol in methylene chloride) followed by crystallization from ether gave 8-chloro-6-(2-chlorophenyl)-3,4-dihydro-3-hydroxypyrrolo[3,4-d][2]benzazepin-1(2H)-one as pale yellow prisms, mp 221°–222° C.

EXAMPLE 43

8-Chloro-6-(2-chlorophenyl)-1,4-dihydro-1-hydroxypyrrolo[3,4-d][2]benzazepin-3(2H)-one In one portion, 0.35 g (1 mmol) of 8-chloro-6-(2-chlorophenyl)-1,4-dihydropyrrolo[3,4-d][2]benzazepin-3(2H)-one was added to an ice-cooled solution of 1.3 g (7.9 mmol) of trichloroacetic acid and 1.0 g (2.2 mmol) of lead tetraacetate in 15 ml of methylene chloride. After stirring for 4 hours, the mixture was neutralized with saturated aqueous sodium bicarbonate solution. The methylene chloride solution was washed with water, dried over anhydrous sodium sulfate and concentrated at reduced pressure to a yellow residue. Purification of the residue by column chromatography (silica gel, 10 g; eluent, 5% methanol in methylene chloride) followed by crystallization from ether gave 8-chloro-6-(2-chlorophenyl)-1,4-dihydro-1-hydroxypyrrolo[3,4-d][2]benzazepin-3(2H)-one as pale yellow prisms, mp 247°–249° C.

EXAMPLE 44

8-Chloro-6-(2-chlorophenyl)pyrrolo[3,4-d][2]benzazepin-1,3-(2H,4H)-dione,
8-chloro-6-(2-chlorophenyl)-3,4-dihydro-3-hydroxypyrrolo[3,4-d][2]benzazepin-1(2H)-one and
8-chloro-6-(2-chlorophenyl)-1,4-dihydro-1-hydroxypyrrolo[3,4-d][2]benzazepin-3(2H)-one In one portion, 5.0 g (15.2 mmol) of 8-chloro-6-(2-chlorophenyl)-2H,4H-pyrrolo[3,4-d][2]benzazepine were added to a cooled solution of 20.0 g (120 mmol) of trichloroacetic acid and 14.0 g (31.6 mmol) of lead tetraacetate in 50 ml of methylene chloride. The mixture was stirred at room temperature for 4 hours and then diluted with methylene chloride and water. The methylene chloride solution was washed with saturated aqueous sodium bicarbonate solution, dried over anhydrous sodium sulfate and concentrated at reduced pressure to a green residue. Purification of the residue by column chromatography (silica gel, 100 g; eluent, 5% methanol in methylene chloride) gave in the first product band after crystallization from ether 8-chloro-6-(2-chlorophenyl)pyrrolo[3,4-d][2]benzazepin-1,3-(2H,4H)-dione as yellow prisms, mp 224°–225° C.

Further elution gave in the second product band after crystallization from ether 8-chloro-6-(2-chlorophenyl)-3,4-dihydro-3-hydroxypyrrolo[3,4-d][2]benzazepin-1(2H)-one as pale yellow prisms, mp 222°–223° C.

Still further elution gave in the third product band after crystallization from ether 8-chloro-6-(2-chlorophenyl)-1,4-dihydro-1-hydroxypyrrolo[3,4-d][2]benzazepin-3(2H)-one as pale yellow prisms, mp 247°–249° C.

EXAMPLE 45

8-Chloro-6-(2-chlorophenyl)-1-acetoxy-1,4-dihydropyrrolo[3,4-d][2]benzazepin-3(2H)-one,
8-chloro-6-(2-chlorophenyl)-3-acetoxy-3,4-dihydropyrrolo[3,4-d][2]benzazepin-1(2H)-one and
8-chloro-6-(2-chlorophenyl)-2H,4H-pyrrolo[3,4-d][2]benzazepine-1,3-diol diacetate Portionwise, 12.0 g (27 mmol) of lead tetraacetate were added over 2 hours to a solution of 6.0 g (12.2 mmol) of 8-chloro-6-(2-chlorophenyl)-2H,4H-pyrrolo[3,4-d][2]benzazepine in 120 ml of acetic acid. After stirring for an additional 2 hours, hydrogen sulfide gas was bubbled into the solution. The resulting precipitate was removed by filtration over Celite. The filtrate was neutralized by the addition of saturated aqueous sodium carbonate solution and extracted with methylene chloride. The methylene chloride solution was washed with water, dried over anhydrous sodium sulfate and concentrated at reduced pressure to give a brown oil. Purification by column chromatography (silica gel, 100 g; eluent, 100% methylene chloride to 20% ether in methylene chloride gradient) gave in the first product band an off-white solid. Recrystallization from a mixture of methylene chloride, ether, and petroleum ether gave 8-chloro-6-(2-chlorophenyl)-2H,4H-pyrrolo[3,4- d][2]benzazepine-1,3-diol diacetate as colorless needles, mp 189°–190° C.

Further elution gave 1.95 g of a foam which crystallized from a mixture of ether and petroleum ether to give 8-chloro-6-(2-chlorophenyl)-3-acetoxy-3,4-dihydropyrrolo[3,4-d][2]benzazepin-1(2H)-one as colorless prisms, mp 172°–174° C.

Continued elution gave fine needles. Recrystallization from a mixture of ether and methylene chloride gave 8-chloro-6-(2-chlorophenyl)-1-acetoxy-1,4-dihydropyrrolo[3,4-d][2]benzazepin-3(2H)-one, mp 219°–221° C.

EXAMPLE 46

8-Chloro-6-(2-chlorophenyl)-3,4-dihydro-3-methoxypyrrolo[3,4-d][2]benzazepin-1(2H)-one methanesulfonate A solution of 0.6 g of 8-chloro-6-(2-chlorophenyl)-3-acetoxy-3,4-dihydropyrrolo[3,4-d][2]benzazepin-1(2H)-one and 3 ml of a 1 M methanolic solution of methanesulfonic acid in 10 ml of methanol was stirred at room temperature for 30 minutes. The solution was concentrated at reduced pressure to half the volume, diluted with ether, and the resulting precipitate was collected by filtration to give orange crystals. Recrystallization from a mixture of methanol and ether gave 8-chloro-6-(2-chlorophenyl)-3,4-dihydro-3-methoxypyrrolo[3,4-d][2]benzazepin-1(2H)-one methanesulfonate as off-white prisms, mp 157°–160° C.

EXAMPLE 47

8-Chloro-6-(2-chlorophenyl)-1,4-dihydro-1-methoxypyrrolo[3,4-d][2]benzazepin-1(2H)-one methanesulfonate A solution of 0.1 g (0.25 mmol) of 8-chloro-6-(2-chlorophenyl)-3-acetoxy-3,4-dihydropyrrolo[3,4-d][2]benzazepin-1(2H)-one and 1 ml of a 1 M methanolic solution of methanesulfonic acid was allowed to stand at room temperature for 36 hours. The mixture was diluted with ether, and the resulting precipitate was collected by filtration to give 8-chloro-6-(2-chlorophenyl)-1,4-dihydro-1-methoxypyrrolo[3,4-d][2]benzazepin-1(2H)-one methanesulfonate. Recrystallization from a mixture of ether and methanol gave fine needles, mp 185°–187° C.

EXAMPLE 48

8-Chloro-6-(2-chlorophenyl)-3-(benzoyloxy)-3,4-dihydropyrrolo[3,4-d][2]benzazepin-1(2H)-one A solution of 0.3 g (0.9 mmol) of 8-chloro-6-(2-chlorophenyl)-3-hydroxy-3,4-dihydropyrrolo[3,4-d][2]benzazepin-1(2H)-one, 0.3 g (1.3 mmol) of benzoic acid anhydride, and 0.3 g (2.5 mmol) of dimethylaminopyridine in a mixture of 30 ml of methylene chloride and 10 ml of tetrahydrofuran was stirred at 0° C. for 1 hour. The mixture was diluted with water, washed successively with cold, dilute hydrochloric acid, saturated aqueous sodium bicarbonate solution, and brine and dried over anhydrous sodium sulfate. The methylene chloride solution was concentrated at reduced pressure. The residue was purified by column chromatography (silica gel, 10 g; eluent, 5% ether in methylene chloride) to give 8-chloro-6-(2-chlorophenyl)-3-(benzoyloxy)-3,4-dihydropyrrolo[3,4-d][2]benzazepin-1(2H)-one as colorless crystals. Recrystallization from ether gave colorless crystals, mp 140°–142° C.

EXAMPLE 49

| | TABLET FORMULATION (Direct compression) | | | | |
|---|---|---|---|---|---|
| Item | Ingredients | mg/tablet | mg/tablet | mg/tablet | mg/tablet |
| 1. | 8-chloro-6-(2-chlorophenyl)-1,4-dihydropyrrolo[3,4-d][2]benzazepin-3(H)—one or 8-chloro-6-(2-chlorophenyl)-1,4-dihydro-1-methylpyrrolo[3,4-d][2]benzazepin-3(H)—one | 1 | 5 | 10 | 25 |
| 2. | Lactose | 221 | 217 | 212 | 181 |
| 3. | Avicel | 45 | 45 | 45 | 55 |
| 4. | Direct Compression Starch | 30 | 30 | 30 | 35 |
| 5. | Magnesium Stearate | 3 | 3 | 3 | 4 |
| | Weight of tablet | 300 mg | 300 mg | 300 mg | 300 mg |

Procedure:
1. Mix Item 1 with an equal amount of lactose. Mix well.
2. Mix with Items 3 and 4 and the remaining amount of Item 2. Mix well.
3. Add magnesium stearate and mix for 3 minutes.
4. Compress on a suitable press equipped with appropriate punches.

EXAMPLE 50

| | TABLET FORMULATION (Wet granulation) | | | | |
|---|---|---|---|---|---|
| Item | Ingredients | mg/tablet | mg/tablet | mg/tablet | mg/tablet |
| 1. | 8-chloro-6-(2-chlorophenyl)-1,4-dihydropyrrolo[3,4-d][2]benzazepin-3(H)—one or 8-chloro-6-(2-chlorophenyl)-1,4-dihydro-1-methylpyrrolo[3,4-d][2]benzazepin-3(H)—one | 1 | 5 | 10 | 25 |
| 2. | Lactose | 202 | 232 | 261 | 280 |
| 3. | Modified Starch | 25 | 35 | 45 | 55 |
| 4. | Pregelatinized Starch | 20 | 25 | 30 | 35 |
| 5. | Distilled Water q.s. | — | — | — | — |
| 6. | Magnesium Stearate | 3 | 3 | 4 | 5 |
| | Weight of tablet | 250 mg | 300 mg | 350 mg | 400 mg |

Procedure:
1. Mix Items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 51

| | CAPSULE FORMULATION | | | | |
|---|---|---|---|---|---|
| Item | Ingredients | mg/tablet | mg/tablet | mg/tablet | mg/tablet |
| 1. | 8-chloro-6-(2-chlorophenyl)-1,4-dihydropyrrolo[3,4-d][2]ben- | 1 | 5 | 10 | 25 |

CAPSULE FORMULATION

| Item | Ingredients | mg/tablet | mg/tablet | mg/tablet | mg/tablet |
|------|-------------|-----------|-----------|-----------|-----------|
|      | zazepin-3(H)—one or 8-chloro-6-(2-chlorophenyl)-1,4-dihydro-1-methylpyrrolo[3,4-d][2]benzazepin-3(H)—one | | | | |
| 2.   | Lactose     | 203       | 293.5     | 328       | 372.5     |
| 3.   | Starch      | 30        | 35        | 40        | 30        |
| 4.   | Talc        | 15        | 15        | 20        | 20        |
| 5.   | Aerosol OT  | 1         | 1.5       | 2         | 2.5       |
|      | Capsule fill weight | 250 mg | 350 mg | 400 mg | 450 mg |

Procedure:
1. Mill Items 1, 2, 3, and 5 in a suitable mixer. Mill.
2. Add talc and mix well.
3. Encapsulate on suitable equipment.

EXAMPLE 52

A solution of 1.5 g (3.4 mmol) of 8-chloro-6-(2-chlorophenyl)-2H,4H-pyrrolo[3,4-d][2]benzazepine-1,3-diol diacetate in 25 ml of a 1 M methanol solution of methanesulfonic acid was refluxed for 6 hours. The reaction was cooled, made basic by the addition of saturated aqueous sodium bicarbonate and extracted with methylene chloride. The methylene chloride solution was dried over anhydrous sodium sulfate and concentrated at reduced pressure. The residue was dissolved in 4 ml of a 1 M methanol solution of methanesulfonic acid, diluted with ether until turbid and filtered. The filtrate was made basic with saturated aqueous sodium bicarbonate. The ether solution was dried over anhydrous sodium sulfate and concentrated at reduced pressure to give the free base of the product as off white crystals, mp. 192°–194° C. The presence of the isomeric 8-chloro-6-(2-chlorophenyl)-1,4-dihydro-1-methoxypyrrolo[3,4-d][2]benzazepin-3-one was noted by the thin layer chromatography but was not isolated.

The methanesulfonate salt of 8-chloro-6-(2-chlorophenyl)-1,4-dihydro-3-methoxypyrrolo[3,4-d][2]benzazepin-1(2H)-one was prepared by dissolving the free base in an excess of methanolic methanesulfonic acid and isolated by precipitating the salt with the addition of ether. Recrystallization from a mixture of methanol and ether gave the salt as colorless crystals, mp. 157°–160° C.

What is claimed:

1. A compound of the formula

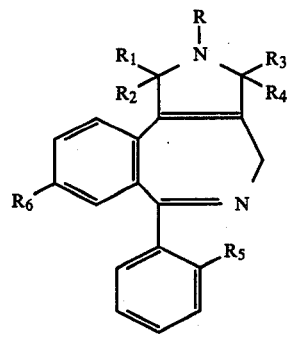

wherein $R_1$ and $R_3$ are selected from the group consisting of hydrogen, lower alkyl, hydroxy, lower alkoxy or

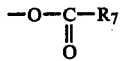

and $R_2$ and $R_4$ are hydrogen or $R_1$ and $R_2$ and/or $R_3$ and $R_4$ taken together are oxo groups with the proviso that at least one oxo group is present; R is selected from the group consisting of hydrogen, lower alkyl, $C_2$ to $C_7$ carboxylic acids and the lower alkyl esters, amides and mono or di lower alkyl amides thereof, hydroxy $C_2$ to $C_7$ alkyl and amino $C_2$ to $C_7$ alkyl or mono- or di-lower alkyl amino $C_2$ to $C_7$ alkyl; $R_5$ is halogen or hydrogen and $R_6$ is halogen with the proviso that when $R_1$ or $R_3$ is hydroxy, lower alkoxy or

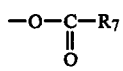

then R is lower alkyl or hydrogen; $R_7$ is $C_1$ to $C_6$ alkyl, phenyl, or hydrogen the N-oxides and the pharmaceutically acceptable salts thereof.

2. A compound of the formula

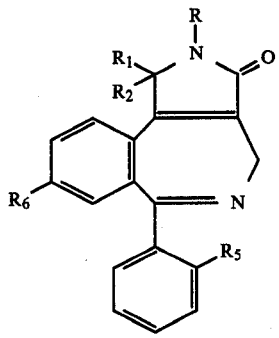

wherein $R_1$ is selected from the group consisting of hydrogen, lower alkyl, lower alkoxy, hydroxy or

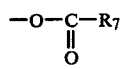

and $R_2$ is hydrogen or $R_1$ and $R_2$ taken together are an oxo group; R is selected from the group consisting of hydrogen, lower alkyl, $C_2$ to $C_7$ carboxylic acids and the lower alkyl esters, amides and mono or di lower alkyl amides thereof, hydroxy $C_2$ to $C_7$ alkyl and amino $C_2$ to $C_7$ alkyl or mono- or di-lower alkylamino $C_2$ to $C_7$ alkyl; $R_5$ is halogen or hydrogen and $R_6$ is halogen with the proviso that when $R_1$ or $R_3$ is hydroxy, lower alkoxy or

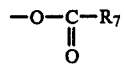

then R is lower alkyl or hydrogen; $R_7$ is $C_1$ to $C_6$ alkyl, phenyl, or hydrogen and the pharmaceutically acceptable salts thereof.

3. A compound as claimed in claim 3 wherein $R_2$ is hydrogen.

4. A compound of the formula

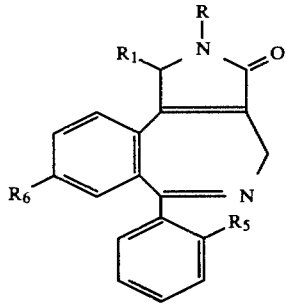

wherein $R_1$ is selected from the group consisting of hydrogen or lower alkyl; R is selected from the group consisting of hydrogen, lower alkyl, $C_2$ to $C_7$ carboxylic acids and the lower alkyl esters, amides and mono or di lower alkyl amides thereof, hydroxy $C_2$ to $C_7$ alkyl and amino $C_2$ to $C_7$ alkyl or mono- or di-lower alkyl amino $C_2$ to $C_7$ alkyl; $R_5$ is halogen or hydrogen and $R_6$ is halogen.

5. A compound of the formula

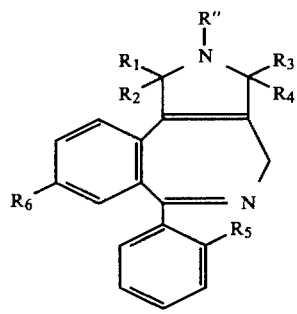

wherein R" is selected from the group consisting of hydrogen or lower alkyl; $R_1$ and $R_3$ are selected from the group consisting of hydrogen, lower alkyl, lower alkoxy, hydroxy or

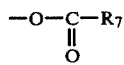

and $R_2$ and $R_4$ are hydrogen or $R_1$ and $R_2$ and/or $R_3$ and $R_4$ taken together are oxo groups with the proviso that at least one oxo group is present; $R_5$ is hydrogen or halogen and $R_6$ is halogen; $R_7$ is $C_1$ to $C_6$ alkyl, phenyl, or hydrogen.

6. A compound of the formula

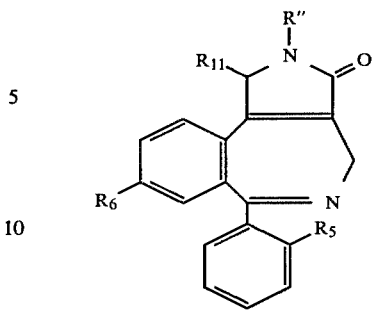

wherein R" and $R_{11}$ are selected from the group consisting of hydrogen or lower alkyl and $R_5$ and $R_6$ are halogen.

7. A compound selected from the group consisting of
8-chloro-6-(2-fluorophenyl)-3,4-dihydropyrrolo[3,4-d][2]benzazepin-1(2H)-one,
8-chloro-6-(2-chlorophenyl)-3,4-dihydropyrrolo[3,4-d][2]benzazepin-1(2H)-one,
8-chloro-3,4-dihydro-6-phenylpyrrolo[3,4-d][2]benzazepin-1(2H)-one or
8-chloro-6-(2-chlorophenyl)-3,4-dihydro-2-methylpyrrolo[3,4-d][2]benzazepin-1(2H)-one.

8. A compound selected from the group consisting of
8-chloro-6-(2-chlorophenyl)-1,4-dihydro-1-hydroxypyrrolo[3,4-d][2]benzazepin-3(2H)-one,
8-chloro-6-(2-chlorophenyl)-3,4-dihydro-3-hydroxypyrrolo[3,4-d][2]benzazepin-1(2H)-one or
8-chloro-6-(2-chlorophenyl)pyrrolo[3,4-d][2]benzazepin-1,3-(2H,4H)-dione.

9. A compound selected from the group consisting of
8-chloro-6-(2-chlorophenyl)-1,4-dihydropyrrolo[3,4-d][2]benzazepin-3(2H)-one-5-oxide or
8-chloro-6-(2-chlorophenyl)-3,4-dihydropyrrolo[3,4-d][2]benzazepin-1(2H)-one-5-oxide.

10. The compounds selected from the group consisting of:
8-chloro-6-(2-chlorophenyl)-1-ethyl-1,4-dihydropyrrolo[3,4-d][2]benzazepin-3(2H)-one,
8-chloro-6-(2-chlorophenyl)-1,4-dihydro-1-methyl-3-oxo-2H-pyrrolo[3,4-d][2]benzazepine-2-acetic acid methyl ester,
8-chloro-6-(2-chlorophenyl)-1,4-dihydro-1-methyl-3-oxo-2H-pyrrolo[3,4-d][2]benzazepine-2-acetamide and
8-chloro-6-(2-chlorophenyl)-1,4-dihydro-1-methylpyrrolo[3,4-d][2]benzazepin-3(2H)-one.

11. The compound:
8-chloro-6-(2-fluorophenyl)-1,4-dihydropyrrolo[3,4-d][2]benzazepin-3(2H)-one.

12. The compound:
8-chloro-1,4-dihydro-6-phenylpyrrolo[3,4-d][2]benzazepin-3(2H)-one.

13. The compound:
8-chloro-6-(2-chlorophenyl)-1,4-dihydro-1,2-dimethylpyrrolo[3,4-d][2]benzazepin-3(2H)-one.

14. The compound:
8-chloro-6-(2-chlorophenyl)-1,4-dihydro-2-(2-hydroxyethyl)-1-methylpyrrolo[3,4-d][2]benzazepin-3(2H)-one.

15. The compound:
8-chloro-6-(2-chlorophenyl)-1,4-dihydropyrrolo[3,4-d][2]benzazepin-3(2H)-one.

16. The compound:
8-chloro-6-(2-chlorophenyl)-1,4-dihydro-1-methylpyrrolo[3,4-d][2]benzazepin-3(2H)-one.

17. The compound:
8-chloro-6-(2-chlorophenyl)-1,4-dihydro-2-methylpyrrolo[3,4-d][2]benzazepin-3(2H)-one.

* * * * *